United States Patent [19]

Kotilainen et al.

[11] Patent Number: 4,885,156

[45] Date of Patent: Dec. 5, 1989

[54] MOUTHWASH SOLUTION

[75] Inventors: Risto M. Kotilainen, Kuopio; Kaj R. Lilius, Espoo, both of Finland

[73] Assignee: Suomen Calcusan Oy-Finska Calcussan AB, Finland

[21] Appl. No.: 165,280

[22] PCT Filed: Jul. 7, 1987

[86] PCT No.: PCT/FI87/00092

§ 371 Date: Mar. 2, 1988

§ 102(e) Date: Mar. 2, 1988

[87] PCT Pub. No.: WO88/00044

PCT Pub. Date: Jan. 14, 1988

[30] Foreign Application Priority Data

Jul. 8, 1986 [FI] Finland ............................ 862881

[51] Int. Cl.$^4$ .............................................. A61K 7/16
[52] U.S. Cl. .............................. 424/54; 424/49; 424/10
[58] Field of Search .................. 424/49, 52, 54, 10

[56] References Cited

U.S. PATENT DOCUMENTS

| | | |
|---|---|---|
| 2,975,102 | 3/1961 | Matsumura et al. ............... 424/54 |
| 3,004,897 | 10/1961 | Shore ................................. 424/54 |
| 3,699,221 | 10/1972 | Schole et al. ...................... 424/54 |
| 3,937,807 | 2/1976 | Haefele .............................. 424/44 |
| 3,988,434 | 10/1976 | Schole et al. ...................... 424/54 |
| 4,130,638 | 12/1978 | Dhabhar et al. ................... 424/49 |
| 4,177,258 | 12/1979 | Gaffar et al. ...................... 424/52 |
| 4,183,915 | 1/1980 | Gaffar et al. ...................... 424/52 |
| 4,224,310 | 9/1980 | Shah .................................. 424/54 |
| 4,436,721 | 8/1984 | Gaffar ................................ 424/52 |
| 4,606,912 | 8/1986 | Rudy et al. ........................ 424/52 |

FOREIGN PATENT DOCUMENTS

| | | |
|---|---|---|
| 80/00057 | 7/1980 | PCT Int'l Appl. . |
| 490384 | 8/1938 | United Kingdom . |
| 86/03674 | 7/1986 | World Int. Prop. O. ........... 424/54 |

*Primary Examiner*—Shep K. Rose
*Attorney, Agent, or Firm*—Steinberg & Raskin

[57] ABSTRACT

A mouthwash solution to prevent enrichment, in the oral cavity on mucous membranes and dental surfaces, of metals, particularly heavy metals. The mouthwash solution contains water-soluble alkali metal or alkali earth metal salt or salts, particularly the Na, K, Mg or Ca salt, or their complex salt of an amino(carboxylic) acid forming with heavy metal ions stable, water-soluble complex compounds in oral cavity conditions.

1 Claim, No Drawings

MOUTHWASH SOLUTION

BACKGROUND OF THE INVENTION

The present invention concerns a mouthwash solution intended to prevent enrichment of heavy metals in the oral cavity on mucous membranes and dental surfaces.

In corrective dental care metallic materials are used in rather great profusion, such as tooth fillings and crown materials; the number of different materials is estimated to be more than one hundred. Usually these materials are composed of four or five different metals and compounds thereof.

For metallic filling material is used amalgam filling, which is typically prepared of mercury (contribution about 45–55%) and of a premix, which typically has had the composition: Ag 67–70%, Sn 25–29%, Cu 0–5%, Zn 0–2%. In modern amalgam fillings, however, copper tends, owing to price considerations, to replace silver, its quantity rising even up to 30%.

Actual prostheses, i.e., crowns, are made outside the oral cavity by casting a metal duplicate corresponding in its structure to the extracted tooth, or a metal blank which is overlaid with ceramic enamel to simulate the structure of the tooth. High-gold materials have traditionally been the best material to serve this purpose. In order to replace gold and to optimize the properties of the alloy (mechanical characteristics, castability, corrosion resistance, metal/ceramic bond, thermal expansion) other metals, also less noble ones, have to be added (Pt, Pd, Ag, Cu, Fe, Sn, Zn, In, Ga, etc.). The composition of the materials which are used and the contribution of base metals vary considerably both from manufacturer to maunfacturer and in accordance with the requirements imposed on the prosthesis.

The problem in dental care of the kind just described have been allergic reactions of patients, especially in risk groups like asthmatics, who on the whole are disposed to allergic reactions. The cause responsible for these reactions is the dissolving of heavy metals in the mouth from dental care materials. These heavy metal effusions tend to become enriched and to accumulate in the oral cavity on dental surfaces, darkening them, and particularly on mucuous membranes.

We have found that those patients in whom allergic symptoms have been observed have in their saliva and in their oral cavity metal residues in quantities which should be reduced. In our studies we have established the cause of certain diseases of the oral mucous membranes to be allergic irritation from metals. It is also likely that contact allergy in the oral cavity may acerbate the cell picture of incipient cancer of the mouth.

We have observed in our studies that all metals here in question cause allergies of the oral cavity. One patient may moreover simultaneously have allergies from several metals.

Nobler metals and noble metal-based homogeneous metal alloys are not in themselves likely to react with saliva, which a weak electrolyte and one of which the acidity is close to neutral.

The situation is substantially changed, in principle, when there are concomitantly several metallic materials in the mouth which differ as to their electrochemical nature.

The difference between metals in electrochemical respect is commonly described with the aid of the so-called electrochemical potential series, which gives a simple picture of the differential potentials acting between different metals. Thus, for instance, when gold and copper are in mutual contact said differential potential tends to dissolve copper, which in itself would be comparatively stable in the circumstances.

The amount in which heavy metals are dissolved in saliva is dependent on a number of factors, e.g. on how direct is the contact between the metals, and on the homogenity of the alloy. Even from an alloy rich in noble metals there may be even rapid dissolving in saliva of components which are only little less noble. Of course, conditions for dissolution of heavy metals are particularly favourable in connection with tooth filling, burnishing and bridge and crown grinding and thereafter.

SUMMARY OF THE INVENTION

The object of the present invention is to prophylactically prevent allergic reactions started by heavy metals and the darkening of dental surfaces, by preventing enrichment and accumulation of heavy metal ions in the oral cavity.

The mouthwash solution of the invention is, in order to achieve this, characterized in that it contains water-soluble alkali metal or earth alkali metal salt or salts, in particular Na, K, Mg or Ca salt, or their combination salt or a mixture thereof, of an amino(carboxylic) acid or acids forming with heavy metal ions stable, water-soluble complex compounds in the conditions prevailing in the oral cavity.

The salt is preferably 2Na-Ca-EDTA, Mg salt of EDTA, Na salt of NTA, or Na salt of EDTA. In other words, the salt is preferably a salt of an amino(carboxylic) acid.

Additionally, the acidity, i.e. the pH of the mouthwash solution, has preferably been adjusted. More specifically, the solution is adjusted so that the pH range is within about 5.5–8.5, more preferably between about 6.5–7.5. Furthermore, the content of the salt in the mouthwash solution is preferably about 1–10%, more preferably about 2–5%.

The mouthwash solution of the invention is used by washing the oral cavity frequently enough with a solution containing an appropriate quantity of a substance which binds the heavy metals in stable, water-soluble complex salts, preferably in chelates. With such treatment, the heavy metals will be eliminated from the organism after washing, together with the washing water, and owing to the short duration of the treatment the metallic filling and prosthetic materials, or the enamel surfaces of the teeth, suffer no damage. However, a more intensive treatment may even be recommendable in connection with tooth filling or burnishing and with bridge or crown grinding.

A very great number of compounds efficiently complexing heavy metal ions are known. A considerable number of these act very selectively, that is, they complex only metal ions of a certain kind and within certain pH ranges and under certain reaction conditions, while other complex formers produce salts of which the stability depends with different metals selectively, though strongly, on the acidity of the solution.

It is important from the viewpoint of the present invention that when selecting a suitable complex former for use in a mouthwash solution, it is checked that it does complex specifically in oral pH conditions those heavy metals which are desired. Tables exist which serve this purpose. The complex salt should moreover be water-soluble under the conditions in this case.

In most instances, however, as was observed before and as noted above, many metals cause allergies and one patient may be simultaneously allergic to several metals. Usually there is also no accurate information about the heavy metals spectrum in the oral cavity at the particular time.

Thus, it is advantageous, as taught by the invention, to use complex formers which are active in a broad range. Since chelate (complex) formers with broad action operate as efficient recoverers of heavy metal ions in the oral cavity, the invention also affords the advantage that on the basis of the composition of the wash solution a picture is obtained of the heavy metals spectrum in the oral cavity.

DESCRIPTION OF THE PREFERRED EMBODIMENTS

Among broad-action, efficient complex formers, the following may be particularly mentioned: iminodiacetic acid (IDA), nitrilotriacetic acid (NTA), -iminotriacetic acid (ITA), ethylenediamine-N,N'-diacetic acid, ethylenediaminetetraacetic acid (EDTA), diethylenetriaminepentaacetic acid (DPTA), 2-hydroxyethylethylenediaminetriacetic acid (HEDTA), ethylenediamine (En), N,N'-diethylenediamine, diethylenetriamine (Den), diethylenetetraamine (Trien), $\beta,\beta',\beta''$-triaminotriethylamine (Tren), propylenediamine. Further agents which are efficient in broad action are salicylic acid, salicylaldehyde and derivatives, citric acid, acetylacetone, o-aminophenol and condensed phosphates.

Those amino(carboxylic) acids which are important as regards usability are suitable for use towards the purpose of the present invention in the form of a solution in which they occur as alkali or alkali earth salts or complex salts thereof, e.g. 2Na-Ca-EDTA. The acidity of the solution should be compatible with oral environment, neutralizing being most advantageously effected with NaOH. The solution will contain NA-Ca salt of EDTA when neutralizing the $CaH_2$-EDTA solution with NaOH. A substantial part is present in the 2Na-Ca-EDTA form. A typical picture of the properties of amino(carboxylic) acids is given by Table 1. The table reveals that the stability of the complex salts of EDTA depends very strongly, though non-selectively, on the acidity of the solution. Under typically oral conditions (pH=6.5-7.5), EDTA chelate heavy metal ions efficiently. Mercury, the EDTA chelate of which is one of the most stable, is missing in the table.

It is characteristic of EDTA and NTA that when these acids are neutralized e.g. with NaOH there is an exactly determined acidity (pH) of the solution corresponding to any given degree of neutralizing. It is therefore essential to state this, e.g. from the viewpoint of determining the composition of the Na salt.

TABLE 1

| Ph | pM values for EDTA EDTA, 10% excess | | | | | | | | | | |
|---|---|---|---|---|---|---|---|---|---|---|---|
| | $Cu^{2+}$ | $Ni^{2+}$ | $Pb^{2+}$ | $Co^{2+}$ | $Zn^{2+}$ | $Cd^{2+}$ | $Fe^{2+}$ | $Fe^{3+}$ | $Mn^{2+}$ | $Ca^{2+}$ | $Mg^{2+}$ |
| 2 | 3.9 | 4.0 | 3.8 | 2.2 | 2.2 | 2.3 | 2.1 | 10.7 | 2.0 | 2.0 | 2.0 |
| 3 | 6.7 | 6.8 | 6.6 | 4.5 | 4.8 | 3.7 | 3.7 | 13.5 | 2.7 | 2.0 | 2.0 |
| 4 | 8.9 | 9.0 | 8.8 | 6.7 | 6.7 | 7.0 | 5.1 | 15.7 | 4.5 | 2.3 | 2.0 |
| 5 | 10.8 | 10.9 | 10.8 | 8.6 | 8.6 | 9.0 | 7.1 | 17.6 | 6.0 | 3.8 | 2.4 |
| 6 | 12.6 | 12.8 | 12.6 | 10.5 | 10.5 | 10.7 | 8.8 | 19.5 | 7.3 | 5.5 | 3.8 |
| 7 | 13.9 | 14.1 | 13.9 | 11.8 | 11.8 | 12.1 | 10.2 | 20.8 | 9.1 | 6.3 | 4.9 |
| 8 | 15.0 | 15.1 | 14.9 | 12.8 | 12.8 | 13.1 | 11.3 | 21.8 | 10.1 | 7.3 | 5.4 |
| 9 | 16.0 | 16.1 | 15.9 | 13.8 | 13.8 | 14.1 | 12.4 | 22.8 | 11.1 | 8.3 | 6.4 |
| 10 | 16.8 | 17.0 | 16.8 | 14.6 | 14.6 | 15.0 | 14.2 | 23.7 | 12.0 | 9.2 | 7.2 |
| 11 | 17.2 | 17.3 | 17.2 | 15.0 | 15.0 | 15.3 | 16.4 | 25.5 | 12.3 | 9.5 | 7.6 |

In the following an example is presented in which the above-mentioned compounds have been active owing to their broad action spectrum although the background information was most incomplete.

EXAMPLES

Patient 1

A 63 years old housewife attended for investigations because of intensive glossalgic pain and smarting of maxillary gums and buccal and labial mucuosa. There was a slight swelling under her eyes and she complained of unpleasant thickness of the face. The breathing was according to her difficulted because of sinusitis like feeling. These major complaints had lasted for two years, since she had got a ten units long metal-ceramic bridge in the maxilla. Her difficulties began in 1979, when she got a chromium cobalt denture in lower jaw resulting as bleeding allergic ulcerations. After refusing the denture she got a new one at the university clinic with similar results. A new casting with a gold bar was constructed. When this broke during the first month it was based by cold curing acrylic with a bleeding allergic ulceration as a result. Prior to these reactions, only her allergy to nickel was known.

A complete ten units bridge was made by private dentist in the lower jaw from C-gold casting and this was tolerated well. Immediately after this, another ten units bridge was constructed in upper jaw from metal-ceramics. Soon after the insertion severe pains and smarting with descripted symptoms of the head region began. Several root canal treatments and paradental operations were performed by specialists without relief.

When the closer investigation began, her glukose tolerance test and serum B 12 levels showed to be normal. Eosinofile count of the full blood was 525 (normal variation 40-440) and differential leukosyte count 0.13 (variation 0.00-0.07). The serum immunoglobules seemed to be normal: S-IGA 1.7 (0.9-4.5), S-IGG 12.0 (8.0-18.0), S-IGM 1.6 (0.6-2.8).

A 5% Ca-Na-2-EDTA in water solution was introduced for differential diagnostics. She rinsed her mouth twice daily by 10 ml of solution for two minutes. After spitting out she washed her mouth by tap water. Within three days the pain and smarting symptoms disappeared. Within three days the pain and smarting symptoms disappeared. After 3 months, August 1986 the blood controls showed normalization of eosinofiles from 525 to 194 and the differential count of leucosytes from 0.13 to 0.09 according to the eosinofiles. In a second control after three more methods the eosinofile count of leukosytes had gone down to 0.06 and the blood eosinofiles were still at 194.

Prior to the treatment skin patch tests were performed to reveal possible allergies. There were positive reactions to 5% nickel sulfate by 4+, 1% chromium cloride by 3+, 5% tin chloride by 2+, N-Etyl-P-Toluensulfoamide by 2+ and P-tolydietanolamine by 2+. Because of the supposed irritation to tin instead of allergy, the tin concentration was diluted to 2.5 and 1%, which did not alter the reading of the patch test.

On the absolute request of the patient, the upper bridge was taken off and constructed again of a traditional C-gold alloy. She felt well with this material. On further request, the composition of the ceramic metal was analyzed at the Technical University of Helsinki by an Energy Dispersive Roentgen Spectrophotometry with a semiquantitative result of the non casted alloy containing 4.8% tin and the casted and oxidated alloy containing site dependent variations of great amounts of tin. The ceramic was shown to contain 8-10% tin, the richer sites being on the colored cervical areas, where the mixture of metal oxides was used as characterization. In addition, the ceramic contained maximum 1% nickel on some points of the surface. The content of copper was varying between 1-3%.

Patient 2

A 24 years old man had been in hospital investigations four years before because of atopic reactions and asthma. He was found to be allergic to hay and pollens. Two years later this man with red hair got recurrent aphthous stomatitis and swelling around his eyes. The lower lip was swollen and anaesthetic. He was referred to ear and nose clinic where a suspicion diagnosis remained for Melkerson-Rosenthal syndrome or sarcoidosis. During the next two years he had daily a slight rise in temperature, he felt tired and was suffering itching gingival pains and headache.

In blood tests the leukosyte count was 3.6, of which eosinofiles counted 2%. Wholeblood eosinofiles counted 44 (variation 40-440). Patch tests for allergy were performed from the Swedish dental tray of Kemoteknik by specialist in dermatology. Positive tests were achieved by 30% propylene glycol (2+) and tin chloride 5% (2+). The skin reactions were interpreted as weak allergic reactions.

When his anamnestic data were reviewed, he told that about five days after each visit at his dentist the reactions came. He had received several silver amalgam fillings or crowns of amalgam.

One lower molar was extracted and a marked amalgam tattoo was seen at place. In biopsy of the pigment only foreign body reactions were seen witout allergic findings. Gingival margins in lower jaw were slightly hyperplastic without gingivitis. In biopsy of this gingiva, no inflammation or foreign body reaction was seen.

A metal antagonist therapy by chelating mouth rinse was performed by twice a day rinsing. This preparation was calcium saturated Ca-Na-2-EDTA solution with no activity to calcium ions. After the first week of treatment the gingival smarting disappeared, the patient had no fever and felt well. Mouthrinsing was performed for two months. No aphthous attacks or other symptoms have appeared. Patient's symptoms are concluded to be connected to the silver amalgam fillings or other irritation of metallic nature.

We claim:

1. In a method for preventing enrichment of metals, in an oral cavity on mucous membranes and dental surfaces, the improvement comprising the step of
administering to patients allergic to metals dissolving from their metallic amalgam with fillings, bridges, crowns, dentures, or other prostheses until the patients' symptoms of allergic reaction to the metal are concluded, a mouthwash solution containing at least one water-soluble alkali metal or alkali earth salt of an amino(carboxylic) acid selected from the group consisting of salts of iminodiacetic acid (IDA), nitrilotriacetic acid (NTA) or iminotriacetic acid (ITA), ethylenediamine-N,N'-diacetic acid, ethylenediaminetetraacetic acid (EDTA), diethylene-triaminepentaacetic acid (DPTA), 2-hydroxyethylethylenediamine-triacetic acid (HEDTA), ethylenediamine (EN), N,N'-diethylenediamine, diethylene-triamine (DEN), diethylenetetraamine (TRIEN), beta,beta',beta''-triamino-triethylamine (TREN), propylenediamine, salicylic acid, salicylaldehyde and derivatives thereof, citric acid, acetylacetone, o-aminophenyl, and condensed phosphates, and mixtures thereof,
in an amount effective in twice a day mouthrinse for forming, with heavy metal ions, stable, water-soluble complex compounds under oral cavity conditions.

* * * * *